(12) United States Patent
Huber et al.

(10) Patent No.: US 11,214,690 B2
(45) Date of Patent: Jan. 4, 2022

(54) PEARLESCENT PIGMENTS, PROCESS FOR PRODUCING THEM, AND USE OF SUCH PIGMENTS

(71) Applicant: Schlenk Metallic Pigments GmbH, Roth (DE)

(72) Inventors: Adalbert Huber, Bensheim (DE); Fabian Piech, Wendelstein (DE); Kaiman Shimizu, Roth (DE)

(73) Assignee: Schlenk Metallic Pigments GmbH

( * ) Notice: Subject to any disclaimer, the term of this patent is extended or adjusted under 35 U.S.C. 154(b) by 0 days.

(21) Appl. No.: 15/566,248

(22) PCT Filed: Apr. 15, 2016

(86) PCT No.: PCT/EP2016/000624
§ 371 (c)(1),
(2) Date: Oct. 13, 2017

(87) PCT Pub. No.: WO2016/165832
PCT Pub. Date: Oct. 20, 2016

(65) Prior Publication Data
US 2018/0112076 A1 Apr. 26, 2018

(30) Foreign Application Priority Data
Apr. 15, 2015 (EP) .................... 15001083

(51) Int. Cl.
| C09C 1/00 | (2006.01) |
| C08K 3/22 | (2006.01) |
| C08K 3/36 | (2006.01) |
| C09D 7/40 | (2018.01) |
| A61K 8/02 | (2006.01) |
| A61K 8/26 | (2006.01) |
| C03C 1/04 | (2006.01) |
| C08K 9/02 | (2006.01) |
| C09D 5/36 | (2006.01) |
| C09D 11/037 | (2014.01) |

(52) U.S. Cl.
CPC .......... C09C 1/0051 (2013.01); A61K 8/0262 (2013.01); A61K 8/26 (2013.01); C03C 1/04 (2013.01); C08K 3/22 (2013.01); C08K 3/36 (2013.01); C08K 9/02 (2013.01); C09C 1/0009 (2013.01); C09D 5/36 (2013.01); C09D 7/70 (2018.01); C09D 11/037 (2013.01); C01P 2004/04 (2013.01); C01P 2004/24 (2013.01); C01P 2004/54 (2013.01); C08K 2003/2227 (2013.01); C08K 2003/2265 (2013.01); C09C 2200/1004 (2013.01); C09C 2200/1054 (2013.01); C09C 2200/301 (2013.01); C09C 2200/302 (2013.01); C09C 2200/303 (2013.01); C09C 2220/106 (2013.01)

(58) Field of Classification Search
CPC ................ C09C 1/0051; C09C 1/0009; C09C 2200/1004; C09C 2200/1054; C09C 2200/301; C09C 2200/302; C09C 2200/303; C09C 2220/106; C09D 7/70; C09D 5/36; C09D 11/037; A61K 8/0262; A61K 8/26; C03C 1/04; C08K 9/02; C08K 2003/2227; C01P 2004/04; C01P 2004/24; C01P 2004/54
See application file for complete search history.

(56) References Cited

U.S. PATENT DOCUMENTS

| 3,926,659 | A | * | 12/1975 | Bernhard | ................ A61K 8/29 |
| | | | | | 106/418 |
| 4,328,042 | A | | 5/1982 | Ostertag et al. | |
| 4,542,182 | A | | 9/1985 | Schuppiser | |
| 4,565,581 | A | * | 1/1986 | Bernhard | ............. C09C 1/0015 |
| | | | | | 106/417 |
| 5,277,711 | A | | 1/1994 | Schmidt | |
| 5,607,504 | A | | 3/1997 | Schmid | |
| 5,624,486 | A | | 4/1997 | Schmid | |
| 5,964,936 | A | | 10/1999 | Reisser | |
| 5,972,098 | A | | 10/1999 | Andes | |
| 6,398,999 | B1 | | 6/2002 | Josephy | |
| 6,432,535 | B1 | | 8/2002 | Noguchi | |
| 6,599,355 | B1 | | 7/2003 | Darmstadt | |
| 6,776,835 | B2 | | 8/2004 | Darmstadt | |
| 7,452,597 | B2 | | 11/2008 | Bujard | |
| 7,828,890 | B2 | | 11/2010 | Henglein | |
| 7,943,194 | B2 | | 5/2011 | Bujard | |
| 8,524,261 | B2 | * | 9/2013 | Schmidt | ................. C09C 3/063 |
| | | | | | 424/401 |
| 8,647,429 | B2 | | 2/2014 | Melson | |
| 8,846,783 | B2 | | 9/2014 | Rathschlag | |
| (Continued) | | | | | |

FOREIGN PATENT DOCUMENTS

| CN | 101445675 A | 6/2009 |
| DE | 9400447 U1 | 8/1994 |
| (Continued) | | |

OTHER PUBLICATIONS

Patent Cooperation Treaty (PCT), International Search Report and Written Opinion for Application PCT/EP2016/000624 filed Apr. 15, 2016, dated Aug. 2, 2016, International Searching Authority, EP.
(Continued)

*Primary Examiner* — Pegah Parvini
(74) *Attorney, Agent, or Firm* — McDonald Hopkins LLC (57) ABSTRACT

The present invention relates to semitransparent pearlescent pigments, to processes for producing them, and to the use of such pearlescent pigments, where the pearlescent pigments comprise monolithically constructed substrate platelets composed of a metal oxide having an average thickness of 1 to 40 nm and a form factor, expressed by the ratio of the mean size to the average thickness, of at least 80, which are enveloped by at least one substantially transparent coating A composed of at least one low-index metal oxide and/or metal oxide hydrate, having a refractive index of less than 1.8, and at least one interference layer in the form of a coating B composed of at least one high-index metal oxide, having a refractive index of at least 1.8.

11 Claims, 3 Drawing Sheets

(56) References Cited

U.S. PATENT DOCUMENTS

| | | | |
|---|---|---|---|
| 2002/0160194 A1 | 10/2002 | Philips | |
| 2003/0005859 A1* | 1/2003 | Andes | C09C 1/0033 |
| | | | 106/403 |
| 2003/0008120 A1 | 1/2003 | Andes | |
| 2003/0209169 A1 | 11/2003 | Andes et al. | |
| 2004/0244640 A1 | 12/2004 | Vogt et al. | |
| 2005/0013934 A1 | 1/2005 | Xiong | |
| 2005/0176850 A1 | 8/2005 | Schmidt | |
| 2005/0223940 A1 | 10/2005 | Seeger et al. | |
| 2005/0260352 A1* | 11/2005 | Maul | B05D 7/08 |
| | | | 427/402 |
| 2007/0104663 A1 | 5/2007 | Henglein et al. | |
| 2007/0199478 A1 | 8/2007 | Eckart | |
| 2007/0259182 A1* | 11/2007 | Bujard | B82Y 30/00 |
| | | | 428/405 |
| 2010/0047199 A1 | 2/2010 | Eckart | |
| 2012/0219607 A1 | 8/2012 | Schmidt | |
| 2015/0098972 A1 | 4/2015 | Schumacher | |
| 2016/0168387 A1* | 6/2016 | Shimizu | A61K 8/0266 |
| | | | 106/404 |

FOREIGN PATENT DOCUMENTS

| | | |
|---|---|---|
| DE | 19836810 A1 | 2/2000 |
| DE | 102007062942 A1 | 6/2008 |
| EP | 0033457 B1 | 5/1983 |
| EP | 0806457 A2 | 11/1997 |
| EP | 1072651 | 1/2001 |
| EP | 1072651 A1 | 1/2001 |
| EP | 1564261 | 8/2005 |
| EP | 1564261 A2 | 8/2005 |
| EP | 1621585 A2 | 2/2006 |
| EP | 1621586 A1 | 2/2006 |
| EP | 2 799 397 * 5/2014 | C01F 7/02 |
| EP | 2799397 A2 | 11/2014 |
| JP | H0616965 | 1/1994 |
| JP | H0693206 | 4/1994 |
| JP | H08209024 | 8/1996 |
| JP | H09249442 | 9/1997 |
| JP | H11510552 | 9/1999 |
| JP | 2002522618 | 7/2002 |
| JP | 2002528639 | 9/2002 |
| JP | 2003113330 | 4/2003 |
| JP | 2006506518 | 2/2006 |
| JP | 2006527779 | 12/2006 |
| JP | 2007511655 | 5/2007 |
| JP | 2008511704 | 4/2008 |
| JP | 2010185073 | 8/2010 |
| JP | 2012513508 | 6/2012 |
| JP | 2013064053 | 4/2013 |
| JP | 2014218424 | 11/2014 |
| KR | 1020040047972 | 6/2004 |
| KR | 1020050006248 | 1/2005 |
| RU | 2404220 C2 | 11/2010 |
| RU | 2434908 C2 | 11/2011 |
| WO | 00/34395 A1 | 6/2000 |
| WO | 2004055119 A1 | 7/2004 |
| WO | 2004/113455 A2 | 12/2004 |
| WO | 2005/049739 A2 | 6/2005 |
| WO | WO2011/045030 | 6/2005 |
| WO | 2006/021528 A2 | 3/2006 |
| WO | 2006/066825 A2 | 6/2006 |
| WO | 2006114171 A1 | 11/2006 |
| WO | 2007053409 A2 | 5/2007 |
| WO | 2009/083176 A1 | 7/2009 |
| WO | 2011045030 A1 | 4/2011 |
| WO | 2011095326 A1 | 8/2011 |
| WO | WO2011/095326 | 8/2011 |
| WO | 2013156327 A1 | 10/2013 |
| WO | 2015014484 | 2/2015 |
| WO | 2015014484 A1 | 2/2015 |

OTHER PUBLICATIONS

Japan Patent Office (JPO), Notification of Reasons for Rejection for Patent Application No. 2017-553424, drafted Dec. 20, 2019, dated Jan. 7, 2020, Third Patent Examination Department, Japan.

* cited by examiner

PEARLESCENT PIGMENTS, PROCESS FOR PRODUCING THEM, AND USE OF SUCH PIGMENTS

CROSS-REFERENCE TO RELATED APPLICATION

This application is a 35 U.S.C. 371 national stage filing of PCT Application No. PCT/EP2016/000624 filed on Apr. 15, 2016, which claims priority to European Patent Application No. 15001083.3, filed on Apr. 15, 2015, each of which are incorporated herein in their entirety by reference.

The present invention relates to semitransparent pearlescent pigments, to processes for producing them, and to the use of pearlescent pigments of this kind.

Luster pigments, especially metallic luster pigments or metallic effect pigments, find broad application in many areas of the art. They are used, for example, for coloring paints, printing inks, liquid inks, plastics, glasses, ceramic products, and decorative cosmetic preparations. Of particular economic significance is the use of metallic luster pigments in automobile finishes. On account of their uncopiable optical effects, they are also employed in the production of forgeproof securities and documents such as banknotes, cheques, bank cards, credit cards, entry cards, and tickets. They are distinguished in particular by their attractive, angle-dependent color impression (goniochromaticity) and by their metallike luster.

With conventional pigments, a color impression is produced simply by absorption of particular wavelengths of incident light, and scattered reflection. Common metallic effect pigments reflect the incident light to a high degree and give rise to a light/dark flop, but not to any impression of color. In the case of specific pearlescent pigments, however, optical interference effects mean that a color impression is produced. Pearlescent (pearl luster) pigments of this kind, based generally on at least singly coated platelet-shaped substrates, exhibit interference effects as a result of superimposition of rays of light which are refracted and reflected differently. White light incident on the planar surface of the coated substrates is partly reflected at the outer surface of the coating. The other part is refracted, and reflected at interfaces, as between coating and substrate surface, for example, and refracted again. There is therefore a superimposition of light rays with different phases. Interference of the reflected light produces a color impression. In view of the dependence of the phase difference on the angle of incidence/angle of observation, the color impression as well is angle-dependent. This effect of color change between different reflection angles is referred to as color flop. Factors influencing the phase difference include the thickness of the coating(s), allowing the resultant color impression to be adjusted by way of the coating thickness.

Among the longest-known interference pigments, also called pearlescent pigments, is natural pearl essence; because of the recovery and the associated high costs, however, the part played by pearl essence is a minor one. Besides monocrystalline pearlescent pigments containing lead, such as basic lead carbonate or lead hydrogen phosphate, nontoxic pearlescent pigments in particular have awoken increased interest. Examples in this regard may include pigments based on bismuth oxychloride, which are notable for high luster and good hiding power. Bismuth oxychloride, however, has low light stability and can be offered in paste form. A further disadvantage is the low mechanical robustness.

The most widespread pearlescent pigments are those consisting of interference layers applied to a substrate. The interference layers consist of metal oxides such as titanium dioxide or iron oxide, for example. Suitable substrates include natural or synthetic mica, glass flakes, aluminum oxide flakes, silicon dioxide, or metallic flakes.

Interference pigments based on transparent, platelet-shaped substrates, such as mica, silicon dioxide or aluminum oxide, which carry a high-index coating, consisting of $TiO_2$, are described in EP 1 564 261 A2. The platelet-shaped substrates have an average thickness of between 0.02 and 2 µm, preferably between 0.1 and 1 µm, and more preferably between 0.2 and 0.8 µm. In order to obtain an intensive color effect with superimposed, angle-dependent color tinting, the average thickness of the individual platelets must be situated within a standard deviation of <15%.

WO 2011/095326 A1 describes effect pigments based on uncoated or coated, platelet-shaped substrates which have an outer, calcined coating containing metal oxide, the pigments comprising different metal oxides. With regard to the dimensions of the platelet-shaped substrates, WO 2011/095326 A1 describes how substrates of usual size can be used, without imposing particular requirements. On account of this outer coating, these effect pigments have a high stability even without corresponding subsequent coatings.

EP 1 072 651 A1 describes pigments based on thin flakes having an average particle size of 0.5 µm to 10 µm, preferably 2 µm to 8 µm, which are coated initially with spherical $SiO_2$ particles and subsequently with ultrafine $TiO_2$ particles. On account of their soft-focus effect, among others, pigments of this kind are added as fillers to cosmetic formulations, for example. Through the spherical structure of the $SiO_2$ and $TiO_2$ particles, reflection is substantially undirected, evoking an unwanted whitening effect in cosmetic application on the skin.

A comparable application is described for the pearlescent pigments disclosed in WO 2011/045030 A1. These pearlescent pigments comprise a largely transparent, platelet-shaped, synthetic substrate which is enveloped with an optically active coating, the substrate having an unusually small diameter and a low substrate thickness, with a mean thickness in the range from 40 nm to 110 nm. As a result of this low particle size, situated preferably in a range from 3.0 to 5.0 µm, it is possible to prevent unwanted luster. In view of the low aspect ratio (ratio between substrate diameter and thickness), however, the pearlescent effect is not very pronounced.

There are also pearlescent pigments, moreover, which are based on platelet-shaped metallic substrates having an iron oxide coating. The sizes of the substrate particles are 5 to 100 µm, and the thicknesses between 0.1 µm and 5 µm. Because of the metallic core, however, these pigments have to be stabilized, using particular solvents, for example, in order to diminish their sensitivity with respect to explosive reaction (thermite reaction).

In certain respects, however, the pearlescent pigments known from the prior art have considerable deficiencies. It is fundamentally desirable, for reasons of efficiency to provide pearlescent pigments with high hiding power and high chroma in order to meet the requirements for ever-thinner paint films, as in the automobile industry, for example. A further disadvantage of known pearlescent pigments are the high costs associated with the production processes.

It is an object of the present invention, therefore, to provide a flexible and cost-effective process for producing environmentally compatible pearlescent pigments, and also to provide corresponding pearlescent pigments, which are to have high hiding power, good stability, and, at the same time, excellent chroma (chromaticity).

This object is achieved by means of the embodiments specified in the claims.

Provided in particular is a process for producing semitransparent pearlescent pigments, comprising the steps of
providing monolithically constructed metallic substrate platelets having an average thickness of 1 to 40 nm and a form factor, expressed by the ratio of the mean size to the average thickness, of at least 80,
coating the metallic substrate platelets with an enveloping, substantially transparent coating A composed of at least one low-index metal oxide and/or metal oxide hydrate, having a refractive index of less than 1.8, coating the thus-coated metallic substrate platelets with at least one interference layer in the form of a coating B composed of at least one high-index metal oxide, having a refractive index of at least 1.8,
the coating steps taking place by hydrolytic decomposition of one or more organometallic compounds and/or by precipitation of one or more dissolved metal salts, and subsequently calcining the thus-coated substrate platelets at 550 to 1200° C., preferably at 600 to 1200° C., to convert the metallic substrate platelets into the corresponding metal oxide.

In an alternative embodiment, the process of the invention may be carried out in the following modified order:
providing monolithically constructed metallic substrate platelets having an average thickness of 1 to 40 nm and a form factor, expressed by the ratio of the mean size to the average thickness, of at least 80,
coating the metallic substrate platelets with an enveloping, substantially transparent coating A composed of at least one low-index metal oxide and/or metal oxide hydrate, having a refractive index of less than 1.8,
subsequently calcining the thus-coated substrate platelets at 550 to 1200° C., preferably at 600 to 1200° C., to convert the metallic substrate platelets into the corresponding metal oxide, and
thereafter coating the calcined substrate platelets with at least one interference layer in the form of a coating B composed of at least one high-index metal oxide, having a refractive index of at least 1.8,
the coating steps taking place by hydrolytic decomposition of one or more organometallic compounds and/or by precipitation of one or more dissolved metal salts.

Through the process of the invention it is possible to produce, flexibly and cost-effectively, semitransparent pearlescent pigments which have a high hiding power, good stability, and, at the same time, excellent chroma (chromaticity). More particularly it is possible by means of the production process of the invention to produce semitransparent pearlescent pigments reproducibly in large quantities, with simplicity and flexibility, the pigments being distinguished by high optical quality.

"Semitransparent" for the purposes of the present invention refers to a $\Delta E$ value of $1<\Delta E<50$, with $\Delta E$ being measured according to DIN 55987. The measurement of $\Delta E$ according to DIN 55987 is accomplished here by applying a coating film, comprising the pearlescent pigment of the invention with a mass fraction of 12 wt % (dry weight), to each of a black and a white surface. The film thickness of the dried coating is 12 µm. Thereafter a determination is made of the total color difference $\Delta E$ between the coatings on the black and white grounds. In the case of a transparent coating B (when using $TiO_2$, for example), the low thickness of the substrate results in a high chroma at the interference angle (15° from the specular).

The semitransparent pearlescent pigments generated by the process of the invention feature monolithically constructed substrate platelets composed of a metal oxide having an average thickness of 1 to 40 nm and a form factor (aspect ratio of the substrate), expressed by the ratio of the mean size to the average thickness, of at least 80, the substrate platelets being enveloped by at least one substantially transparent coating A composed of at least one low-index metal oxide and/or metal oxide hydrate, having a refractive index of less than 1.8, and the substrate platelets also having, enveloping them or arranged thereon, at least one interference layer in the form of a coating B composed of at least one high-index metal oxide, having a refractive index of at least 1.8.

The pearlescent pigments of the invention can be produced cost-effectively. They have an unusually high hiding power and hence offer diverse advantages for their use, as paint in the automobile and vehicle industry, for example. In comparison to conventional pearlescent pigments, moreover, the pearlescent pigments according to the present invention are notable for excellent chromaticity.

The substrate platelets have an average thickness of at most 40 nm, preferably less than 40 nm, more preferably at most 25 nm, as for example at most 20 nm. The average thickness of the substrate platelets is at least 1 nm, preferably at least 2.5 nm, more preferably at least 5 nm, as for example at least 10 nm. Preferred ranges for the thickness of the substrate platelets are 2.5 to 40 nm, 5 to 40 nm, 10 to 40 nm, 2.5 to 30 nm, 5 to 30 nm, 10 to 30 nm, 2.5 to 25 nm, 5 to 25 nm, 10 to 25 nm, 2.5 to 20 nm, 5 to 20 nm, and 10 to 20 nm. Preferably each substrate platelet has an extremely uniform thickness. As a result of production, however, there may be fluctuations in thickness within a platelet. Such fluctuations ought preferably to amount to no more than ±50%, based on the average thickness of the platelet in question, more preferably at most ±25%, very preferably at most ±10%, especially preferably at most ±5%. The average thickness here refers to the numerical mean of maximum and minimum thickness. Determining the minimum and maximum layer thicknesses is accomplished by measurement on the basis of a transmission electron micrograph (TEM) of a (coated) substrate platelet (cf. FIG. 1). Since the color of the coated substrate platelets is dependent on the layer thickness, a precise and uniformly established thickness of the uncoated substrate platelets ensures a uniform color effect.

With regard to the fluctuation in the layer thickness and to the determination of the (average) layer thickness, the observations above are also valid, analogously, for the thicknesses of the coatings A and B and also, if present, C.

Where reference is made here to the "thickness" of a coating or of a substrate platelet, the thickness in question is considered to be the average thickness, unless otherwise defined at the relevant point.

The substrate platelets are monolithic in construction. Monolithic in this context means consisting of a single, self-contained unit without fractures, stratifications or inclusions. This applies both to the metallic substrate platelets and to the oxidized substrate platelets after the calcining step. The oxidized substrate platelets are preferably homogeneous in construction, meaning that there is substantially no concentration gradient within the platelets. In particular, the oxidized substrate platelets are not laminar in construction and have no particulates or particles distributed therein.

In particular they do not have a core-shell construction, the shell consisting, for example, of one material suitable for the substrate platelets, and the core of a different material, such as a silicon oxide, for example. As a result of their simple construction, the substrate platelets can be produced cost-effectively and efficiently. In contrast to this, a more complex, nonmonolithic construction on the part of the substrate platelets implies a more difficult, time-consuming and cost-intensive production operation.

The mass fraction of the substrate platelet as a proportion of the coated substrate platelet is preferably at most 25 wt %, more preferably at most 20 wt %, as for example at most 15 wt %. However, the mass fraction of the substrate platelets ought not to fall below 1 wt %, preferably not below 2 wt % or 3 wt %. With particular preference, the mass fraction of the substrate platelet as a proportion of the coated substrate platelet is 5 to 12 wt %.

As a result of the low thickness and/or low mass fraction of the substrate platelets, the pearlescent pigment of the invention exhibits particularly high hiding power and high chroma. Furthermore, in view of the low thickness/low mass fraction of the substrate platelets, expensive and scarce materials such as specific transition metals can also be used, resource-sparingly and economically, as material for the substrate platelets.

Aside from the thickness, the size of the uncoated substrate platelets is specified in that the form factor (aspect ratio), expressed by the ratio of the mean size to the average thickness, is at least 80, preferably at least 200, more preferably at least 500, very preferably more than 750. In accordance with the present invention, the mean size of the uncoated substrate platelets is understood as the $d_{50}$ of the uncoated substrate platelets. The $d_{50}$ herein, unless otherwise indicated, is determined using a Sympatec Helos instrument with Quixel wet dispersing. For sample preparation in this case, the sample under investigation is predispersed in isopropanol for a time of 3 minutes.

Accordingly, the size of the uncoated substrate platelets is not critical and can be brought into line with the particular intended application, as long as the form factor is at least 80. For example, the mean size $d_{50}$ of the uncoated substrate platelets is about 2 to 200 µm. According to one preferred embodiment, the mean size $d_{50}$ of the uncoated substrate platelets is 5 to 100 µm, the lower limit being more preferably at least 8 µm and very preferably at least 10 µm. The upper limit, according to one particularly preferred embodiment, is 50 µm, more particularly 30 µm. The mean size $d_{50}$ of the uncoated substrate platelets is in particular between 2 and 50 µm, more preferably between 5 and 30 µm. Depending on intended use, however, as industrial paint, for example, the mean size $d_{50}$ of the uncoated substrate platelets may have a value of around 70 µm, for example. Where the mean size $d_{50}$ of the uncoated substrate platelets is about 2 µm, it is clear for a skilled person to select a correspondingly lower upper limit for the average thickness of the uncoated substrate platelets (presently: 25 nm). The same applies to the corresponding preferred lower limits.

The coated substrate platelets preferably have a total thickness of 50 to 800 nm, more preferably 100 to 700 nm, especially preferably 130 to 400 nm, as for example 150 to 350 nm. Because of the low thickness of the substrate platelets, the pearlescent pigment of the invention exhibits particularly high hiding power and chroma. The low total thickness of the coated substrate platelets is achieved in particular by the low thickness of the uncoated substrate platelets, but also by the setting of the thicknesses of the coatings A and, if present C at an extremely low level. Since the thickness of coating B determines the color impression conveyed by the pearlescent pigment, there is no room for maneuver in this regard when a desired color effect has been stipulated.

The assumption hitherto was that essentially nontransparent (opaque) materials, such as metals, for example, were suitable as substrate platelets, in order to obtain high hiding power. Moreover, it was technically not possible to produce inorganic substrates with low layer thicknesses (below 200 nm). Furthermore, it was assumed that there was a certain minimum thickness below which it was not possible to go, for reasons including the risk of fracture, which would result in a greatly lowered hiding power on the part of the resultant luster pigment.

It has nevertheless been possible to find that with (partially or wholly transparent, i.e., semitransparent) substrate platelets having a layer thickness of at most 40 nm, preferably at most 25 nm, it is possible to produce pearlescent pigments which have a significantly higher hiding power and chroma than conventional metallic luster pigments. The reason for this is probably that a higher surface coverage of the pearlescent pigment is obtained, owing to the low total thickness of the coated substrate platelets. Since the coated substrate platelets are thin, a greater surface area can be covered with the same mass of pigment. As a result of this advantageous effect, the greater transparency of thin, wholly or partially transparent substrate platelets is more than compensated, resulting ultimately in a higher hiding power and/or a higher chroma relative to pearlescent pigments whose substrate platelets are thick.

According to the present invention, metallic substrate platelets are used for producing the semitransparent pearlescent pigments. Metal contemplated includes any metal, semimetal, and metal alloy which can be converted into a corresponding metal oxide in the calcining step of the invention. Such metals include (transition) metals such as, for example, platinum, zinc, chromium, and molybdenum, and also semimetals such as silicon, for example, and also alloys thereof. Preferred metals are aluminum, copper, zinc, and silicon. Preferred substrate platelets are aluminum platelets, copper platelets, and brass platelets, with aluminum platelets being particularly preferred. To promote oxidation of the metallic substrate platelets in the calcining step, the metal platelets may optionally be treated by suitable measures, such as doping, for example.

Modes of production of aluminum platelets include punching from aluminum foil, or common milling and atomizing technologies. Thus, for example, aluminum platelets are obtainable from the Hall process, a wet milling process. Other metal platelets, of bronze, for example, may be obtained in a dry milling process such as the Hametag process.

The aluminum or metal platelets may have various shapes. Examples of substrate platelets which can be used include lamellar and lenticular metal platelets or else vacuum metallized pigments (VMPs). Lamellar metal platelets are distinguished by an irregularly structured edge, and on account of their appearance are also referred to as "cornflakes". Lenticular metal platelets have a substantially regular, round edge, and on account of their appearance are also referred to as "silver dollars". Because of their irregular structure, metallic luster pigments based on lamellar metal platelets generate a greater proportion of scattered light than lenticular metal platelets, whereas with the latter the proportion of reflected light is predominant.

In accordance with the invention, VMPs are used with preference. VMPs may be obtained by the liberation of aluminum from metallized films. They are distinguished by particularly low substrate platelet thickness, in the range from 1 to 40 nm, and by a particularly smooth surface with enhanced reflectivity.

In accordance with the present invention, the metallic substrate platelet in the calcining step is converted substantially completely into the corresponding metal oxide, the substrate platelet in the pearlescent pigment of the invention therefore being present as a monolithic and homogeneous material. This distinguishes the production process of the invention from conventional processes, in which the calcining operations result only in the burning of the outer layer(s). As noted above, the pearlescent pigment obtained in accordance with the invention has no substrate platelets in which only an oxide layer, in the form of a passivation, for example, is formed on the metallic core.

The term "substantially" here, when applied to a constituent of a composition, means that the composition is composed of at least 95 wt %, preferably at least 99 wt %, especially preferably at least 99.5 wt %, approximately 100 wt % for example, of the designated constituent.

The reason why, in accordance with the present invention, the metallic substrate platelet is converted into the corresponding metal oxide lies in particular in the low thickness of the substrate platelet. If the thickness of the substrate platelets is to be greater than 200 nm, it is difficult to obtain complete oxidation of the metallic substrate platelet within the calcining step. The assessment of whether the metallic substrate platelet has undergone conversion to the corresponding metal oxide can be determined preferably by means of transmission electron micrographs (TEM) in combination with energy-dispersive x-ray analysis.

In accordance with the invention, the coated substrate platelets are enveloped by at least one interference layer in the form of a coating B composed of a high-index metal oxide. Between the coating B and the substrate surface, the coated substrate platelets have an enveloping, substantially transparent coating A. The substrate platelets optionally have a further coating C, which is different from the underlying layer B.

Suitable materials for the coatings A, B, and C include all substances which can be applied durably in filmlike manner to the substrate platelets and, in the case of the layers A and B, have the requisite optical properties. In this context, the term "substantially transparent" means that the coatings A transmit at least 70%, preferably at least 80%, especially preferably at least 90% of the incident visible light.

A coating on part of the surface of the coated substrate platelets is generally sufficient to obtain a pearlescent pigment. Thus, for example, only the top and/or bottom side of the platelets may be coated, with the side face(s) being left out. In accordance with the invention, however, the entire surface of the substrate platelets, including the side faces, is covered by coating B. The substrate platelets are therefore completely enveloped by coating B. This improves the optical properties of the pigment of the invention and enhances the mechanical and chemical robustness of the coated substrate platelets. The above is also valid for layer A and also, preferably, for layer C, if present.

Although in each case there may be a plurality of coatings A, B and/or C present, the coated substrate platelets preferably have in each case only one coating A, B, and, if present, C. According to a further preferred embodiment, however, the pearlescent pigments of the invention may have two interference layers in the form of the coating B, such as a combination of iron oxide ($Fe_2O_3$) and $TiO_2$, for example. The coating B is composed of at least one high-index metal oxide. The coating B preferably comprises at least 95 wt %, more preferably at least 99 wt %, approximately 100 wt % for example, of at least one high-index metal oxide.

According to one preferred embodiment, the interference layer in the form of the coating B has a thickness of at least 1 nm, more particularly 5 nm, preferably 20 nm, more preferably at least 40 nm, very preferably at least 50 nm. The thickness of coating B is preferably not more than 250 nm, more preferably at most 150 nm. The thickness of the interference layer in this context means the single layer thickness of the coating B, which is doubled accordingly because of the envelopment in the pearlescent pigment of the invention.

The ratio of the thickness of coating B to the thickness of the uncoated substrate platelets is preferably at least 2, as for example 4, 8 or 10. In principle there is no need to observe any upper limit for this ratio, though for practical reasons it ought to be not more than 1000, preferably not more than 500. The average thickness of a coating or of a substrate platelet is determined from the arithmetic mean of the maximum and minimum thicknesses of the coating/substrate platelet.

Where reference is made here to "substrate platelets", without distinction as to whether they are coated or not, the reference is deemed to refer to uncoated substrate platelets, unless defined otherwise at the relevant point.

In accordance with the invention, between the surface of the substrate platelets and the coating B, there is a further coating A composed of at least one low-index metal oxide (hydrate). According to the present invention, the coating A may be present as a single coating. There may also, however, be two or more substantially transparent coatings A disposed between the coating B and the substrate platelet. The coating A is composed of at least one low-index metal oxide and/or metal oxide hydrate. Coating A preferably comprises at least 95 wt %, more preferably at least 99 wt %, approximately 100 wt % for example, of a low-index metal oxide (hydrate).

The metal oxides which can be used for the coatings A, B, and C occasionally have a certain fraction of secondary constituents and/or impurities. Typical secondary constituents of metal oxides include, in particular, metal hydroxides. For example, a coating of iron oxide may include a certain fraction of iron hydroxide.

The terms "high-index" and "low-index" here each denote materials with a high or low refractive index, respectively. High-index materials have a refractive index of at least 1.8, preferably at least 2.0, and more preferably at least 2.4. Low-index materials have a refractive index of less than 1.8, preferably at most 1.6.

High-index metal oxides suitable for coating B are preferably selectively light-absorbing (i.e., colored) metal oxides, such as, for example, iron(III) oxide (α- and γ-$Fe_2O_3$, red), cobalt(II) oxide (blue), chromium(III) oxide (green), titanium(III) oxide (blue, usually in a mixture with titanium oxynitrides and titanium nitrides), nickel(II) oxide (greenish), copper(I/II) oxide (blue), and vanadium(V) oxide (orange), and also mixtures thereof, though without being confined to these examples. Also suitable are colorless high-index oxides such as titanium dioxide, antimony(III) oxide, zinc(II) oxide and/or zirconium dioxide. The interference layer preferably consists substantially of titanium dioxide or, in the case of colored metal oxides, of iron(III) oxide.

It is preferred, moreover, for the interference layer in the case of colorless oxides to contain corresponding dopants. It is preferred, for example, if the coating B of titanium dioxide comprises dopants selected from tin, aluminum, lithium, zirconium, iron, and cerium, more particularly salts thereof, preferably 0.001 to 5 wt %, more preferably 0.01 to 1 wt %. The interference layer, moreover, may comprise a selectively absorbing dye, preferably 0.001 to 5 wt %, more preferably 0.01 to 1 wt %.

Suitability is possessed by organic and inorganic dyes which can be incorporated stably into a metal oxide coating.

For the rutilization of titanium dioxide, furthermore, there may be a tin dioxide layer applied beneath the titanium dioxide layer. Accordingly, in the pearlescent pigment of the invention, there may be a thin tin dioxide layer, just a few nm thick (<10 nm), between the coating A and the interference layer.

The low-index metal oxides which are suitable for the coating A include, for example, silicon (di)oxide, silicon oxide hydrate, aluminum oxide, aluminum oxide hydrate, cerium oxide, tin oxide ($SnO_2$), and mixtures thereof, preferably silicon dioxide. The thickness of the coating A is commonly 1 to 1000 nm, preferably 5 to 300 nm, more preferably 10 to 150 nm. According to one preferred embodiment, the coating A has a thickness of 5 to 50 nm, more preferably 5 to 40 nm, especially preferably 10 to 40 nm.

As described more precisely below, the thickness of the coating A, and the thickness of the coating B, may be adjusted variably and precisely in accordance with the invention.

In the above-described embodiment wherein the coating A has a thickness of 5 to 50 nm, the distance between the surface of the substrate platelets and the inner surface of coating B is preferably at most 100 nm, more preferably at most 50 nm, especially preferably at most 20 nm. By the thickness of coating A/the distance between the surface of the substrate platelets and coating B being within the range specified above, it is possible to ensure that the coated substrate platelets of the pearlescent pigment of the invention, in the case of colored oxides, have a high hiding power and also a small ΔE. The ΔE is the overall color difference, which in the case of the pearlescent pigments of the invention is preferably at most 25, more preferably at most 20, more particularly at most 15, but in each case always more than 1.

According to a further preferred embodiment, the thickness of the coating A is more than 50 nm. If the layer thickness of the coating A is more than 50 nm, an additional interference effect can be generated in the pearlescent pigment of the invention. The thickness of the coating A may for this purpose be adjusted variably and exactly, in accordance with the materials and dimensions of the substrate platelet and of the further coatings, with the values stated above being valid as a preferred upper limit of the thickness. The additional interference effect, furthermore, may be supported by the use of at least one interference layer harmonized to the thickness of the coating A, and there may also be two or more of these interference layers. In particular in a range from 80 to 200 nm for the layer thickness of the coating A, it is possible, in combination with the interference layer B, to obtain particular color effects.

In accordance with the invention, the pearlescent pigments may have a further coating C, allowing particular surface properties to be set in a targeted way. This coating C, according to one preferred embodiment, is selected from a metal oxide (hydrate), which is different from the underlying coating B, or from organic silane compounds. Examples of organosilanes are propyltrimethoxysilane, propyltriethoxysilane, isobutyltrimethoxysilane, n-octyltrimethoxysilane, isooctyltrimethoxysilane, n-octyltriethoxysilane, n-decyltrimethoxysilane, dodecyltrimethoxysilane, hexadecyltrimethoxysilane, vinyltrimethoxysilane.

Examples of suitable metal oxide (hydrates) are silicon (di)oxide, silicon oxide hydrate, aluminum oxide, aluminum oxide hydrate, zinc oxide, tin oxide, titanium dioxide, zirconium oxide, iron(III) oxide, and chromium(III) oxide. Silicon dioxide is preferred.

The coating C preferably has a thickness of 1 to 500 nm, more preferably of 10 to 500 nm, very preferably 50 to 300 nm.

Although each of the coatings A, B and/or C may be composed of a mixture of two or more metal oxides/oxide hydrates, each of the coatings is preferably composed of a metal oxide (hydrate).

If aluminum is used as metallic substrate platelet material, the amount-of-substance ratio α between oxygen not bonded to aluminum and aluminum, before the calcining step, is preferably at least 3, more preferably at least 4, especially preferably at least 5. If α is at least 3, an amount-of-substance ratio between oxygen not bonded to aluminum and aluminum in a stoichiometric ratio of 3/2 (mol/mol) in the coated substrate platelets is prevented. A mixture of aluminum and oxygen compounds, especially $Fe_2O_3$, in which the amount-of-substance ratio α is in the region of 3/2 may give a strongly exothermic reaction, owing to the high oxophilicity of aluminum metal, in certain circumstances with explosive effect (aluminothermy, thermite reaction). A mixture with α in the region of 3/2 may therefore constitute a safety hazard. The reactivity of such a mixture may be lowered, however, by setting the ratio α at a level which is either much greater or much smaller than 3/2.

As described above, the process of the invention for producing the pearlescent pigments comprises the step of coating the metallic substrate platelets by hydrolytic decomposition of one or more organometallic compounds and/or by precipitation of one or more dissolved metal salts.

Coating A is usefully generated by subjecting organometallic compounds (preferably organic silicon compounds and/or aluminum compounds), in which the organic radicals are bonded to the metals via oxygen atoms, to hydrolysis in the presence of the metallic substrate platelets and of an organic solvent in which the metal compounds are soluble. A multiplicity of organic solvents are suitable for this purpose, with isopropanol being preferred.

Preferred examples of the organometallic compounds are the acetylacetonates and, in particular, alkoxides, especially $C_1$-$C_4$ alkoxides, e.g., aluminum triisopropoxide and tetraethoxysilane (tetraethyl orthosilicate, TEOS).

The hydrolysis is carried out preferably in the presence of a base or an acid as catalyst. Examples of species suitable for this purpose include, in addition to alkali metal hydroxides such as sodium hydroxide, aqueous ammonia solutions in particular. Examples of suitable acidic catalysts are phosphoric acid and organic acids, such as acetic acid and oxalic acid (also called sol-gel process).

Water must be present at least in the quantity required by stoichiometry for the hydrolysis, but the amount is preferably 2 to 100 times, more particularly 5 to 20 times. Based on the amount of water used, preferably 3 to 40 vol %, more preferably 5 to 30 vol %, of a 25 wt % strength aqueous ammonia solution are added.

For temperature management it has proven advantageous to heat the reaction mixture to reflux temperature in steps over the course of 10 to 48 h. When isopropanol is used as solvent, for example, the mixture is stirred preferably first for 4 to 20 h at 40° C., then for 4 to 20 h at 60° C., and finally for 2 to 8 h at 80° C.

In process engineering terms, the coating of substrate platelets with a coating A is accomplished usefully as follows:
substrate platelets, organic solvent, water, and catalyst (acid or preferably base, more particularly, for example, an aqueous ammonia solution) are introduced initially, after which the metal compound for hydrolysis, as a pure substance or in solution, as for example as a 30 to 70, preferably 40 to 60, vol % strength solution in the organic solvent, is added. If the metal compound is added in one step, the suspension is subsequently heated with stirring as described above. Alternatively, the metal compound may be metered in continuously at elevated temperature, in which case water and ammonia may be introduced initially or likewise metered in continuously. After the end of coating, the reaction mixture is cooled back down to room temperature.

In order to prevent agglomeration during the coating procedure, the suspension may be subjected to vigorous mechanical exposure such as pumping, vigorous stirring, or exposure to ultrasound.

The coating step may optionally be repeated one or more times. If the mother liquor has a milky cloudiness to its appearance, it is advisable to replace it prior to further coating.

The metallic substrate platelets jacketed with coating A may be isolated in a simple way by filtration, washing with organic solvent, preferably with the alcohols used as solvents, and subsequent drying (customarily 2 to 24 h at 20 to 200° C.). In accordance with the invention, however, the metallic substrate platelets jacketed with coating A need not be isolated, and can be used in situ for the further coating step.

For the application of the metal oxide layers B, for example, α-iron oxide layers and chromium oxide layers may be applied by hydrolytic decomposition of iron(III) salts such as iron(III) chloride and sulfate or chromium(III) chloride, and subsequent conversion of the resulting hydroxide-containing layers into the oxide layers by heat treatment and/or calcining. Similarly, for example, $TiO_2$ layers may be applied by means of TiOCl. It is also possible for a titanium (III) oxide coating to be achieved by hydrolysis of titanium tetrachloride and subsequent reduction of the resultant titanium dioxide with gaseous ammonia.

If an α-iron oxide layer is intended as metal oxide layer B, this may alternatively be accomplished by gas-phase decomposition of volatile iron pentacarbonyl in the presence of oxygen (oxidative decomposition of $Fe(CO)_5$). Given an appropriate process regime it is then possible, in this specific embodiment, for the oxidative decomposition also to bring about the calcination of the substrate platelets, in other words, for example, the conversion of the Al substrate platelets into $Al_2O_3$ substrate platelets.

If a coating C is required, it may be applied as described for coatings A and B.

Since the sol-gel process is also possible in tanks of variable size, a high product diversity can be realized at low cost. This is a further advantage in comparison to conventional belt coatings, for which the process dictates that the batch sizes are larger.

In accordance with the present invention, the metallic substrate platelets are converted in the calcining step into the corresponding metal oxide. This is done at temperatures of 550 to 1200° C., preferably of 600 to 1200° C., more preferably of 600 to 800° C. Customarily, in this procedure, the substrate platelets are first heated to a temperature of about 450° C. at a rapid heating rate in the range from 3° C./min to 20° C./min, preferably in the range from 5° C./min to 10° C./min. The substrate platelets are subsequently heated from about 450° C. to the actual calcining temperature, in the range from 550° C. to 1200° C., at a heating rate in the range from 0.75° C./min to 3° C./min, preferably 1° C./min to 2° C./min. The calcining is customarily carried out in the above temperature range for a period of 4 h to 12 h. Under these conditions, the metallic substrate platelets are oxidized completely, giving pearlescent pigments having unusually high hiding power (in the case of absorbing interference layers) and chroma (chromaticity). Through the controlled calcination and also the above-described process steps it is possible to provide extremely thin inorganic substrates having improved optical properties.

The calcining step takes place in an oxygen-containing atmosphere, not subject to any particular requirements. For example, the oxygen-containing atmosphere used may be air. It is possible, furthermore, to carry out the calcining step in an atmosphere having an oxygen fraction of, for example, at least 10 vol %.

Surprisingly, the pearlescent pigments of the invention have excellent chroma (chromaticity). The reason for this may possibly be that the fraction of the interference layer as a proportion of the total weight of the pigments is very much greater than in the case of conventional pigments having substantially thicker substrates. In accordance with the present invention, furthermore, it is possible to obtain pearlescent pigments having properties described above, where the substrate thickness is precisely settable and also the further coatings can be applied with precise thicknesses to the substrate.

For assessing the coloristic properties of the pearlescent pigments, angle-dependent lightness measurements can be employed, as described in more detail hereinafter. At a constant incident angle of 45°, the color data are determined as a function of the angle of observation. For determining the coloristic properties of the pearlescent pigments, a paint having a pigment concentration of 6 or 12 wt %, based on the binder, is produced and is coated with a film thickness of 12 μm onto a black plate, by means of a doctor blade. The color data are determined using a Byk-mac from Byk Additive and Instrumente. The angles read off are 15°, 25°, 45°, 75°, and 110° from the specular.

As described above, through the various process steps, it is possible to set exactly the thickness of the metallic substrate platelets and, in conjunction therewith, the thickness of the nonmetallic substrate platelet as well in the pearlescent pigment of the invention. Furthermore, the further coatings can be applied with precise thicknesses to the substrate, to give true optical multilayer systems.

Since, in particular, neither aluminum oxide nor silicon dioxide has an intrinsic color, and the process steps of the invention minimize the incidence of impurities, it is possible to obtain pearlescent pigments having a more pure interference effect. This is an advantage in particular relative to mica-based pearlescent pigments.

By means of the production process of the invention, the coated substrate platelets may first be produced reproducibly in large quantities and in a simple manner. Secondly, completely enveloped pigment particles with a very high quality of the individual coatings (homogeneous, filmlike) can be obtained.

The present invention further relates, in a further aspect, to the use of the above-described pearlescent pigments for coloring paints, printing inks, liquid inks, plastics, glasses, ceramic products, and decorative cosmetic preparations.

The pearlescent pigments of the invention are suitable advantageously for many uses, such as for the coloring of plastics, glasses, ceramic products, decorative cosmetic preparations, and, in particular, liquid inks, printing inks, and security printing inks, and especially paints, for the automobile industry, for example.

For these end applications, the pearlescent pigments of the invention may also be used advantageously in a blend with transparent and hiding white, chromatic, and black pigments, and also with conventional luster pigments based on metal oxide-coated mica pigments and metal pigments, and platelet-shaped iron oxides.

The pearlescent pigments of the invention are cost-effective to produce. They have extremely high hiding power and excellent chromaticity and thus offer diverse advantages for their use, as paint in the automobile and vehicle industry, for example.

Figure 1:
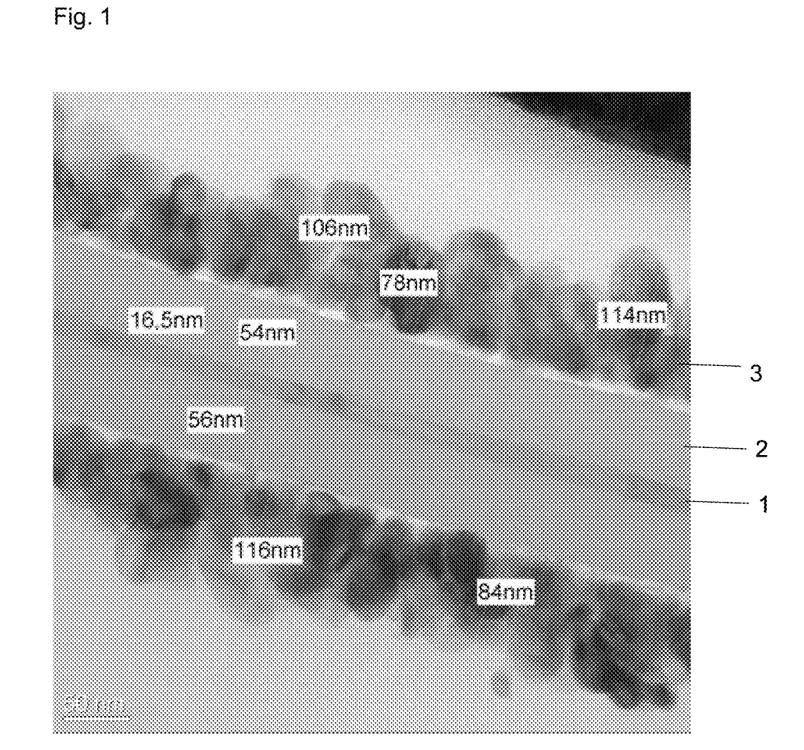

FIG. 1 shows a transmission electron micrograph (TEM) of a coated aluminum oxide platelet of the invention (cf. example 2). The aluminum oxide platelet (1) has a very uniform thickness and is enveloped by an $SiO_2$ layer (2) (coating A, light) and by an iron oxide layer (3) (coating B, dark).

Figure 2:
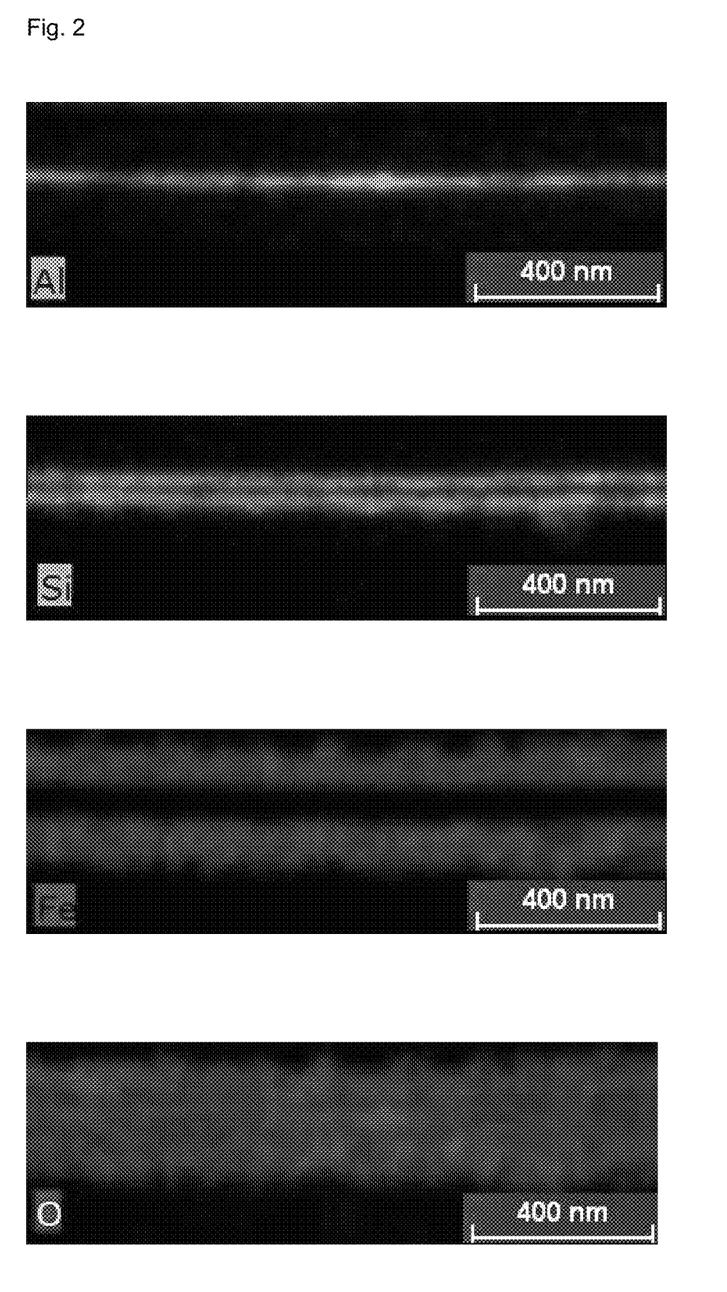

FIG. 2 shows different TEM micrographs of a coated aluminum oxide platelet of the invention in accordance with example 4, extended with energy-dispersive x-ray analysis (EDX, also called energy-dispersive x-ray spectroscopy, EDS). In evidence are (from top to bottom) the scans of aluminum, silicon, iron, and oxygen. It is clearly apparent that the oxygen is also present in the aluminum layer.

Figure 3:
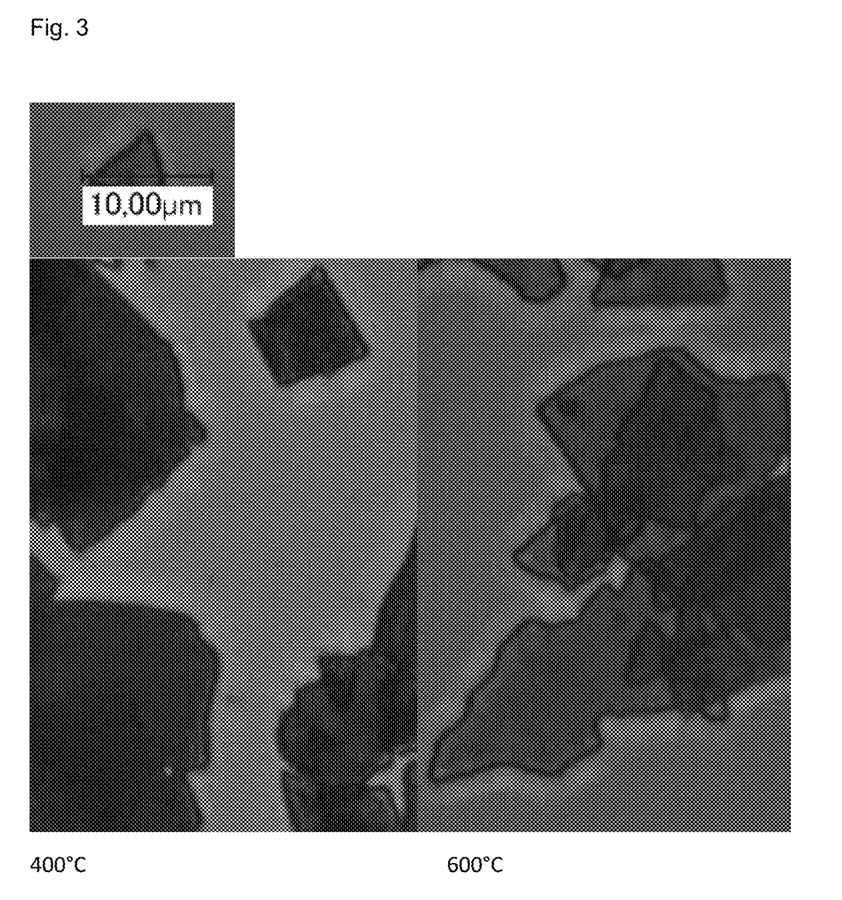

FIG. 3 shows transmitted-light micrographs of an (Al—SiO2-Fe2O3) pigment treated at a temperature of 400° and at 600°. It is clearly apparent that the higher temperature treatment produces a transparency.

The examples below serve as further illustration of the present invention, without being confined thereto.

EXAMPLE 1—THIN ALUMINUM PLATELETS WITH $SiO_2$ (50 NM) AND IRON OXIDE COATING (110 NM)

First of all 10 g of Al platelets (thickness ($t_{50}$) between 10 nm and 20 nm, $d_{50}$=15 μm) were coated with 60 g of $SiO_2$ by means of a sol-gel process using tetraethyl orthosilicate (TEOS). In a round-bottomed flask with reflux condenser and stirrer, these Al platelets were admixed with 500 ml of deionized water and heated to 75° C. with stirring. The pH was adjusted to a level of 3.2 by addition of 10% NaOH solution. The reaction mixture was admixed with 700 g of 40% $FeCl_3$ solution, the pH being kept substantially constant at 3.2 by simultaneous addition of 10% NaOH solution. Following complete addition of the $FeCl_3$ solution, the mixture was stirred for 15 minutes more in order to ensure complete precipitation. The pH was then raised to a level of 7.0 by dropwise addition of 10% NaOH solution over a period of 30 minutes. After 30 minutes of further stirring, the coated pigment was separated from the supernatant reaction solution by filtration, and was washed until salt-free.

The coated aluminum platelets obtained were calcined for 290 minutes at a heating rate of 2° C./minute up to about 600° and sieved with a sieve (mesh size 32 μm). The product obtained was evaluated for its color properties.

EXAMPLE 2—THIN ALUMINUM PLATELETS WITH $SiO_2$ (50 NM) AND IRON OXIDE COATING (100 NM)

First of all 10 g of Al platelets (thickness ($t_{50}$) between 10 nm and 20 nm, $d_{50}$=15 μm) were coated with 60 g of $SiO_2$ by means of a sol-gel process using tetraethyl orthosilicate (TEOS). In a round-bottomed flask with reflux condenser and stirrer, these Al platelets were admixed with 500 ml of deionized water and heated to 75° C. with stirring. The pH was adjusted to a level of 3.2 by addition of 10% NaOH solution. The reaction mixture was admixed with 650 g of 40% $FeCl_3$ solution, the pH being kept substantially constant at 3.2 by simultaneous addition of 10% NaOH solution. Following complete addition of the $FeCl_3$ solution, the mixture was stirred for 15 minutes more in order to ensure complete precipitation. The pH was then raised to a level of 7.0 by dropwise addition of 10% NaOH solution over a period of 30 minutes. After 30 minutes of further stirring, the coated pigment was separated from the supernatant reaction solution by filtration, and was washed until salt-free.

The coated aluminum platelets obtained were calcined for 290 minutes at a heating rate of 2° C./minute up to about 600° and sieved with a sieve (mesh size 32 μm). The product obtained was evaluated for its color properties.

EXAMPLE 3—THIN ALUMINUM PLATELETS WITH $SiO_2$ (15 NM) AND IRON OXIDE COATING (100 NM)

First of all 10 g of Al platelets (thickness ($t_{50}$) between 20 nm and 30 nm, $d_{50}$=20 μm) were coated with 10 g of $SiO_2$ by means of a sol-gel process using tetraethyl orthosilicate (TEOS). In a round-bottomed flask with reflux condenser and stirrer, these Al platelets were admixed with 500 ml of deionized water and heated to 75° C. with stirring. The pH was adjusted to a level of 3.2 by addition of 10% NaOH solution. The reaction mixture was admixed with 400 g of 40% $FeCl_3$ solution, the pH being kept substantially constant at 3.2 by simultaneous addition of 10% NaOH solution. Following complete addition of the $FeCl_3$ solution, the mixture was stirred for 15 minutes more in order to ensure complete precipitation. The pH was then raised to a level of 7.0 by dropwise addition of 10% NaOH solution over a period of 30 minutes. After 30 minutes of further stirring, the coated pigment was separated from the supernatant reaction solution by filtration, and was washed until salt-free.

The coated aluminum platelets obtained were calcined for 290 minutes at a heating rate of 2° C./minute up to about 600° and sieved with a sieve (mesh size 32 μm). The product obtained was evaluated for its color properties.

EXAMPLE 4—THIN ALUMINUM PLATELETS WITH $SiO_2$ (25 NM) AND IRON OXIDE COATING (110 NM)

First of all 10 g of Al platelets (thickness ($t_{50}$) between 10 nm and 20 nm, $d_{50}$=15 μm) were coated with 30 g of $SiO_2$ by means of a sol-gel process using tetraethyl orthosilicate (TEOS). In a round-bottomed flask with reflux condenser and stirrer, these Al platelets were admixed with 500 ml of deionized water and heated to 75° C. with stirring. The pH was adjusted to a level of 3.2 by addition of 10% NaOH solution. The reaction mixture was admixed with 750 g of 40% $FeCl_3$ solution, the pH being kept substantially constant at 3.2 by simultaneous addition of 10% NaOH solution. Following complete addition of the $FeCl_3$ solution, the mixture was stirred for 15 minutes more in order to ensure complete precipitation. The pH was then raised to a level of 7.0 by dropwise addition of 10% NaOH solution over a period of 30 minutes. After 30 minutes of further stirring, the coated pigment was separated from the supernatant reaction solution by filtration, and was washed until salt-free.

The coated aluminum platelets obtained were calcined for 290 minutes at a heating rate of 2° C./minute up to about 600° and sieved with a sieve (mesh size 32 μm). The product obtained was evaluated for its color properties. In FIG. 3 the corresponding TEM micrographs are extended with EDX analysis, demonstrating that the metallic Al substrate platelet is completely oxidized.

EXAMPLE 5—THIN ALUMINUM PLATELETS WITH TITANIUM DIOXIDE COATING

First of all 10 g of Al platelets (thickness between 14 nm and 18 nm, $d_{50}$=14 μm) were coated with 60 g of $SiO_2$ by means of a sol-gel process using tetraethyl orthosilicate (TEOS).

Subsequently 163 g of titanium dioxide were applied by means of TiOCl in 500 ml of water with stirring, at a pH of 2.0 and at 75° C. After the reaction, the pH was raised to 5.5. The coated aluminum flakes produced in this way were filtered and carefully washed and were dried at 120°.

The coated aluminum flakes were subsequently heated to 800° C. at 2° C./minute. After cooling, the completed pigment was additionally sieved with a 25 μm sieve and then subjected to coloristic testing.

EXAMPLE 6—COLORISTIC INVESTIGATIONS

For the coloristic testing, a paint having a pigment concentration of 12 wt % (in the case of masstone pearlescent pigments as per example 1 and example 4—cf. tables 1 and 2) or 6 wt % (in the case of transparent pearlescent pigments as per example 5—cf. table 3), based on the binder, was produced in each case. By means of a doctor blade, a black plate was coated with a film thickness of 12 μm. The color data were determined using a Byk-mac from Byk Additive and Instrumente.

Employed for comparison were commercial pigments from Merck (Iriodin® 502 Red-brown) and from BASF (Mearlin® Exterior CFS Super Copper 3503Z), these being pearl pigments with inorganic substrate based on mica.

The comparison was between pearlescent pigments with virtually the same interference color angle in each case, and the values were contrasted (cf. tables 1 and 2). Critical in this context are the chroma values of the interference (C), and also, in the case of masstone pearlescent pigments, the intensity of the masstone color and the hiding power expressed in the ΔE are important.

Table 1 shows results for masstone pearlescent pigments, with the inventive pearlescent pigments from example 1 being compared with Mearlin® Exterior CFS Super Copper 3503Z from BASF.

Table 2 shows results for masstone pearlescent pigments, with the inventive pearlescent pigments from example 4 being compared with Iriodin® 502 Red-brown from Merck and Mearlin® Exterior CFS Super Copper 3503Z from BASF.

TABLE 1

| | Orange pigments | | | | | | | | |
|---|---|---|---|---|---|---|---|---|---|
| No. | L* 45°/15° | a* 45°/15° | b* 45°/15° | C 45°/15° | L* 45°/45° | a* 45°/45° | b* 45°/45° | C 45°/45° | ΔE 45° |
| 1 | 80.8 | 80.8 | 61.4 | 81.7 | 25.1 | 27.8 | 28.5 | 39.8 | 18.2 |
| Mearlin ® 3503Z | 90.7 | 43.9 | 37.6 | 57.8 | 23.2 | 20.0 | 20.1 | 28.4 | 24.0 |

TABLE 2

| | Orange-red pigments | | | | | | | | |
|---|---|---|---|---|---|---|---|---|---|
| No. | L* 45°/15° | a* 45°/15° | b* 45°/15° | C 45°/15° | L* 45°/45° | a* 45°/45° | b* 45°/45° | C 45°/45° | ΔE 45° |
| 4 | 89.9 | 58.0 | 72.0 | 92.4 | 29.1 | 28.9 | 36.8 | 46.7 | 7.7 |
| Iriodin ® 502 | 92.0 | 92.0 | 47.9 | 66.1 | 21.8 | 20.2 | 21.0 | 29.1 | 27.0 |

From tables 1 and 2 it is evident that the inventive pearlescent pigments, in comparison to commercial pigments and at comparable interference color angles, display significantly higher chroma values.

In particular, the chroma of the masstone color (45°/45°) of example 1 is much higher than the corresponding chroma of the commercial pigment Mearlin® 3503Z. The interference chroma (C 45°/15°) of example 1 as well is improved in comparison to Mearlin® 3503Z.

From the comparison of example 4 with Iriodin® 502, there is again a distinct improvement apparent in the chroma of the masstone color (45°/45°) and also in the interference chroma (C 45°/15°).

The figures in tables 1 and 2, furthermore, demonstrate that the inventive pearlescent pigments in the case of masstone pigments exhibit a particularly low color difference ΔE and hence a particularly high hiding power.

The invention claimed is:

1. A process for producing semitransparent pearlescent pigments, comprising the steps of
    providing monolithically constructed metallic substrate platelets having an average thickness of 1 to 40 nm and a form factor, expressed by the ratio of the mean size to the average thickness, of at least 80,
    coating the metallic substrate platelets with an enveloping, substantially transparent coating A composed of at least one low-index metal oxide and/or metal oxide hydrate, having a refractive index of less than 1.8,
coating the thus-coated metallic substrate platelets with at least one interference layer in the form of a coating B composed of at least one high-index metal oxide, having a refractive index of at least 1.8,
    the coating steps taking place by hydrolytic decomposition of one or more organometallic compounds and/or by precipitation of one or more dissolved metal salts, and
    subsequently calcining the thus-coated substrate platelets at 550 to 1200° C. for a period of 4 hours to 12 hours, to convert the metallic substrate platelets into the corresponding metal oxide where the metallic substrate platelets consist of aluminum, which is then converted completely, in the course of calcining, into aluminum oxide.

2. The process as claimed in claim 1, wherein before the calcining step, in coated substrate platelets, the amount-of-substance ratio α between oxygen not bonded to aluminum and aluminum is at least 3.

3. The process as claimed in claim 1, wherein the coating B is constructed substantially of a high-index metal oxide selected from at least one of iron(III) oxide, cobalt(II) oxide, chromium(III) oxide, nickel(II) oxide, copper(I/II) oxide, vanadium(V) oxide, titanium(III) oxide, titanium dioxide, antimony(III) oxide, zinc(II) oxide and/or zirconium dioxide.

4. The process as claimed in claim 1, wherein the coating A is constructed of at least one coating selected from silicon (di)oxide, silicon oxide hydrate, aluminum oxide, aluminum oxide hydrate, cerium oxide, tin oxide, and mixtures thereof.

5. The process as claimed in claim 1, wherein the metallic substrate platelets used have an average thickness of 25 nm or less.

6. The process as claimed in claim 1, wherein the metallic substrate platelets have a mean size $d_{50}$ of 5 to 100 μm.

7. The process as claimed in claim 1, wherein the average thickness of the coating A is 5 to 50 nm.

8. The process as claimed in claim 1, wherein the average thickness of the coating B is 1 to 250 nm.

9. The process as claimed in claim 1, further comprising the step of providing a further coating C on the coating B, selected from metal oxides, metal oxide hydrates and/or organic silane compounds.

10. The process as claimed in claim 1, wherein the average thickness of the coating A is more than 50 nm.

11. The process for producing semitransparent pearlescent pigments of claim 1, wherein subsequently calcining the thus-coated substrate platelets occurs at 600 to 1200° C. for a period of 4 hours to 12 hours.

* * * * *